(12) United States Patent
Hauck

(10) Patent No.: US 9,237,930 B2
(45) Date of Patent: *Jan. 19, 2016

(54) ROBOTICALLY CONTROLLED CATHETER AND METHOD OF ITS CALIBRATION

(71) Applicant: St. Jude Medical, Atrial Fibrillation Division, Inc., St. Paul, MN (US)

(72) Inventor: John A. Hauck, Shoreview, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/778,893

(22) Filed: Feb. 27, 2013

(65) Prior Publication Data

US 2014/0081290 A1    Mar. 20, 2014

Related U.S. Application Data

(63) Continuation of application No. 13/441,249, filed on Apr. 6, 2012, now Pat. No. 8,407,023, which is a continuation of application No. 11/843,589, filed on Aug. 22, 2007, now Pat. No. 8,155,910, which is a continuation-in-part of application No. 11/139,908, filed on May 27, 2005, now Pat. No. 7,632,265.

(51) Int. Cl.
*G01C 17/38* (2006.01)
*A61B 5/05* (2006.01)
(Continued)

(52) U.S. Cl.
CPC .............. *A61B 19/20* (2013.01); *A61B 1/0052* (2013.01); *A61B 5/042* (2013.01); *A61B 5/7257* (2013.01);
(Continued)

(58) Field of Classification Search
CPC .... A61B 19/20; A61B 19/22; A61B 19/2203; A61B 19/5244; A61B 1/0052; A61B 2017/003; A61B 2017/00699; A61B 2017/00703; A61B 2017/00725; A61B 2017/22075; A61B 2017/3409; A61B 2019/2211; A61B 2019/2242; A61B 2019/2276; A61B 2019/5251; A61B 2019/5253; A61B 2560/0223; A61B 5/042; A61B 5/7257; A61M 25/0105; A61M 25/0133
USPC ........... 702/75, 77, 85, 94, 95, 150, 151, 158, 702/163, 175, 176; 600/301, 374, 407, 424, 600/437, 449, 466, 509, 518, 547, 587; 604/95.01, 95.04, 117, 264, 500, 525, 604/528; 606/1, 28, 41; 607/101, 122, 125, 607/128; 700/249, 260; 128/899

See application file for complete search history.

(56) References Cited

U.S. PATENT DOCUMENTS

| | | |
|---|---|---|
| 4,170,876 A | 10/1979 | Dits et al. |
| 4,510,574 A | 4/1985 | Guittet et al. |

(Continued)

FOREIGN PATENT DOCUMENTS

| | | |
|---|---|---|
| EP | 1779802 | 5/2007 |
| WO | 9744089 | 11/1997 |

(Continued)

OTHER PUBLICATIONS

Extended European Search Report issued in Application No. EP 08 79 8257, dated Aug. 17, 2011.
International Search Report for International Application No. PCT/US2008/073694 Filed Aug. 20, 2008, and Written Opinion Dated Nov. 13, 2008.
International Preliminary Report on Patentability for PCT/US08/73694 filed Aug. 20, 2008, (Oct. 6, 2009).

(Continued)

*Primary Examiner* — John H Le
(74) *Attorney, Agent, or Firm* — Wiley Rein LLP

(57) ABSTRACT

A method of calibrating a robotic device, such as a cardiac catheter, includes oscillating the device on an actuation axis by applying an oscillation vector at an oscillation frequency. While oscillating, a location of the device is periodically measured to generate a plurality of location data points, which may express the location of the device relative to a plurality of measurement axes. The location data points are then processed using a signal processing algorithm, such as a Fourier transform algorithm, to derive a transfer function relating a position of the device to a movement vector for the actuation axis. The transfer function may be resolved into and expressed as a calibration vector for the actuation axis, which may include one or more components, including zero components, directed along each of the measurement axes. The process may be repeated for any actuation axes on which calibration is desired.

17 Claims, 9 Drawing Sheets

(51) Int. Cl.
*A61B 19/00* (2006.01)
*A61B 1/005* (2006.01)
*A61B 5/042* (2006.01)
*A61B 5/00* (2006.01)
*A61B 17/00* (2006.01)
*A61B 17/22* (2006.01)
*A61B 17/34* (2006.01)
*A61M 25/01* (2006.01)

(52) U.S. Cl.
CPC ............ *A61B 19/22* (2013.01); *A61M 25/0133* (2013.01); *A61B 19/2203* (2013.01); *A61B 19/5244* (2013.01); *A61B 2017/003* (2013.01); *A61B 2017/00699* (2013.01); *A61B 2017/00703* (2013.01); *A61B 2017/00725* (2013.01); *A61B 2017/22075* (2013.01); *A61B 2017/3409* (2013.01); *A61B 2019/2211* (2013.01); *A61B 2019/2242* (2013.01); *A61B 2019/2276* (2013.01); *A61B 2019/5251* (2013.01); *A61B 2019/5253* (2013.01); *A61B 2560/0223* (2013.01); *A61M 25/0105* (2013.01)

(56) References Cited

U.S. PATENT DOCUMENTS

| | | | |
|---|---|---|---|
| 4,710,876 | A | 12/1987 | Cline et al. |
| 4,721,114 | A | 1/1988 | DuFault et al. |
| 4,785,399 | A | 11/1988 | Evans et al. |
| 4,837,734 | A | 6/1989 | Ichikawa et al. |
| 4,854,324 | A | 8/1989 | Hirschman et al. |
| 4,873,572 | A | 10/1989 | Miyazaki et al. |
| 4,921,482 | A | 5/1990 | Hammerslag et al. |
| 5,078,140 | A | 1/1992 | Kwoh |
| 5,114,414 | A | 5/1992 | Buchbinder |
| 5,199,950 | A | 4/1993 | Schmitt et al. |
| 5,222,501 | A | 6/1993 | Ideker et al. |
| RE34,502 | E | 1/1994 | Webster |
| 5,275,164 | A | 1/1994 | Maeda et al. |
| 5,281,220 | A | 1/1994 | Blake, III |
| 5,339,799 | A | 8/1994 | Kami et al. |
| 5,368,564 | A | 11/1994 | Savage |
| 5,385,148 | A | 1/1995 | Lesh et al. |
| 5,389,073 | A | 2/1995 | Imran |
| 5,391,147 | A | 2/1995 | Imran et al. |
| 5,391,199 | A | 2/1995 | Ben-Haim |
| 5,396,887 | A | 3/1995 | Imran |
| 5,400,783 | A | 3/1995 | Pomeranz et al. |
| 5,404,638 | A | 4/1995 | Imran |
| 5,406,946 | A | 4/1995 | Imran |
| 5,409,000 | A | 4/1995 | Imran |
| 5,415,166 | A | 5/1995 | Imran |
| 5,423,811 | A | 6/1995 | Imran et al. |
| 5,425,364 | A | 6/1995 | Imran |
| 5,425,375 | A | 6/1995 | Chin et al. |
| 5,431,645 | A | 7/1995 | Smith et al. |
| 5,465,717 | A | 11/1995 | Imran et al. |
| 5,476,100 | A | 12/1995 | Galel |
| 5,478,330 | A | 12/1995 | Imran et al. |
| 5,492,131 | A | 2/1996 | Galel |
| 5,496,311 | A | 3/1996 | Abele et al. |
| 5,498,239 | A | 3/1996 | Galel et al. |
| 5,507,802 | A | 4/1996 | Imran |
| 5,527,279 | A | 6/1996 | Imran |
| 5,533,967 | A | 7/1996 | Imran |
| 5,545,161 | A | 8/1996 | Imran |
| 5,555,897 | A | 9/1996 | Lathrop, Jr. et al. |
| 5,558,073 | A | 9/1996 | Pomeranz et al. |
| 5,578,007 | A | 11/1996 | Imran |
| 5,588,964 | A | 12/1996 | Imran et al. |
| 5,607,462 | A | 3/1997 | Imran |
| 5,632,734 | A | 5/1997 | Galel et al. |
| 5,656,029 | A | 8/1997 | Imran et al. |
| 5,658,278 | A | 8/1997 | Imran et al. |
| 5,662,108 | A | 9/1997 | Budd et al. |
| 5,673,704 | A | 10/1997 | Marchlinski et al. |
| 5,680,860 | A | 10/1997 | Imran |
| 5,681,280 | A | 10/1997 | Rusk et al. |
| 5,697,377 | A | 12/1997 | Wittkampf |
| 5,697,927 | A | 12/1997 | Imran et al. |
| 5,722,401 | A | 3/1998 | Pietroski et al. |
| 5,730,128 | A | 3/1998 | Pomeranz et al. |
| 5,754,741 | A | 5/1998 | Wang et al. |
| 5,782,899 | A | 7/1998 | Imran |
| RE35,880 | E | 8/1998 | Waldman et al. |
| 5,800,482 | A | 9/1998 | Pomeranz et al. |
| 5,808,665 | A | 9/1998 | Green |
| 5,813,991 | A | 9/1998 | Willis et al. |
| 5,820,568 | A | 10/1998 | Willis |
| 5,823,199 | A | 10/1998 | Hastings et al. |
| 5,835,458 | A | 11/1998 | Bischel et al. |
| 5,861,024 | A | 1/1999 | Rashidi |
| 5,876,325 | A | 3/1999 | Mizuno et al. |
| 5,882,333 | A | 3/1999 | Schaer et al. |
| 5,882,346 | A | 3/1999 | Pomeranz et al. |
| 5,895,417 | A | 4/1999 | Pomeranz et al. |
| 5,906,605 | A | 5/1999 | Coxum |
| 5,908,446 | A | 6/1999 | Imran |
| 5,940,240 | A | 8/1999 | Kupferman |
| 5,954,665 | A | 9/1999 | Ben-Haim |
| 5,964,732 | A | 10/1999 | Willard |
| 5,964,796 | A | 10/1999 | Imran |
| 5,971,967 | A | 10/1999 | Willard |
| 5,983,126 | A | 11/1999 | Wittkampf |
| 5,993,462 | A | 11/1999 | Pomeranz et al. |
| 5,997,532 | A | 12/1999 | McLaughlin et al. |
| 6,004,271 | A | 12/1999 | Moore |
| 6,010,500 | A | 1/2000 | Sherman et al. |
| 6,014,579 | A | 1/2000 | Pomeranz et al. |
| 6,015,407 | A | 1/2000 | Rieb et al. |
| 6,032,077 | A | 2/2000 | Pomeranz |
| 6,049,732 | A | 4/2000 | Panescu et al. |
| 6,063,022 | A | 5/2000 | Ben-Haim |
| 6,066,125 | A | 5/2000 | Webster |
| 6,075,871 | A | 6/2000 | Simanovsky et al. |
| 6,083,170 | A | 7/2000 | Ben-Haim |
| 6,089,235 | A | 7/2000 | Hastings et al. |
| 6,096,004 | A | 8/2000 | Megian et al. |
| 6,119,041 | A | 9/2000 | Pomeranz et al. |
| 6,123,699 | A | 9/2000 | Webster |
| 6,197,017 | B1 | 3/2001 | Brock et al. |
| 6,210,362 | B1 | 4/2001 | Ponzi |
| 6,216,027 | B1 | 4/2001 | Willis et al. |
| 6,221,060 | B1 | 4/2001 | Willard |
| 6,227,077 | B1 | 5/2001 | Chiang |
| 6,235,022 | B1 | 5/2001 | Hallock et al. |
| 6,236,883 | B1 | 5/2001 | Ciaccio et al. |
| 6,241,666 | B1 | 6/2001 | Pomeranz et al. |
| 6,258,060 | B1 | 7/2001 | Willard |
| 6,272,371 | B1 | 8/2001 | Shlomo |
| 6,285,898 | B1 | 9/2001 | Ben-Haim |
| 6,289,239 | B1 | 9/2001 | Panescu et al. |
| 6,292,681 | B1 | 9/2001 | Moore |
| 6,298,257 | B1 | 10/2001 | Hall et al. |
| 6,375,471 | B1 | 4/2002 | Wendlandt et al. |
| 6,398,755 | B1 | 6/2002 | Belef et al. |
| 6,432,112 | B2 | 8/2002 | Brock et al. |
| 6,436,107 | B1 | 8/2002 | Wang et al. |
| 6,451,027 | B1 | 9/2002 | Cooper et al. |
| 6,490,474 | B1 | 12/2002 | Willis et al. |
| 6,493,608 | B1 | 12/2002 | Niemeyer |
| 6,500,167 | B1 | 12/2002 | Webster, Jr. |
| 6,516,211 | B1 | 2/2003 | Acker et al. |
| 6,517,477 | B1 | 2/2003 | Wendlandt |
| 6,554,820 | B1 | 4/2003 | Wendlandt et al. |
| 6,554,844 | B2 | 4/2003 | Lee et al. |
| 6,569,160 | B1 | 5/2003 | Goldin et al. |
| 6,572,554 | B2 | 6/2003 | Yock |
| 6,596,084 | B1 | 7/2003 | Patke |
| 6,620,202 | B2 | 9/2003 | Bottcher et al. |
| 6,640,119 | B1 | 10/2003 | Budd et al. |
| 6,650,920 | B2 | 11/2003 | Schaldach et al. |
| 6,658,279 | B2 | 12/2003 | Swanson et al. |

(56) References Cited

U.S. PATENT DOCUMENTS

| | | | |
|---|---|---|---|
| 6,659,956 B2 | 12/2003 | Barzell et al. |
| 6,663,622 B1 | 12/2003 | Foley et al. |
| 6,679,269 B2 | 1/2004 | Swanson |
| 6,679,836 B2 | 1/2004 | Couvillon |
| 6,692,485 B1 | 2/2004 | Brock et al. |
| 6,695,785 B2 | 2/2004 | Brisken et al. |
| 6,699,179 B2 | 3/2004 | Wendlandt |
| 6,716,190 B1 | 4/2004 | Glines et al. |
| 6,718,196 B1 | 4/2004 | Mah et al. |
| 6,719,804 B2 | 4/2004 | St. Pierre |
| 6,726,675 B1 | 4/2004 | Beyar |
| 6,728,562 B1 | 4/2004 | Budd et al. |
| 6,731,976 B2 | 5/2004 | Penn et al. |
| 6,752,800 B1 | 6/2004 | Winston et al. |
| 6,764,450 B2 | 7/2004 | Yock |
| 6,770,027 B2 | 8/2004 | Bunik et al. |
| 6,783,521 B2 | 8/2004 | Ponzi et al. |
| 6,810,281 B2 | 10/2004 | Brock et al. |
| 6,817,974 B2 | 11/2004 | Cooper et al. |
| 6,835,173 B2 | 12/2004 | Couvillon et al. |
| 6,837,867 B2 | 1/2005 | Kortelling |
| 6,843,793 B2 | 1/2005 | Brock et al. |
| 6,858,003 B2 | 2/2005 | Evans et al. |
| 6,860,878 B2 | 3/2005 | Brock |
| 6,872,178 B2 | 3/2005 | Weinberg |
| 6,874,789 B2 | 4/2005 | Shedlov |
| 6,892,091 B1 | 5/2005 | Ben-Haim et al. |
| 6,913,594 B2 | 7/2005 | Coleman et al. |
| 6,926,669 B1 | 8/2005 | Stewart et al. |
| 6,939,309 B1 | 9/2005 | Beatty et al. |
| 6,946,092 B1 | 9/2005 | Bertolino et al. |
| 6,947,785 B1 | 9/2005 | Beatty et al. |
| 6,949,106 B2 | 9/2005 | Brock et al. |
| 6,955,674 B2 | 10/2005 | Eick et al. |
| 6,962,669 B2 | 11/2005 | Foreman et al. |
| 6,974,455 B2 | 12/2005 | Garabedian et al. |
| 6,974,465 B2 | 12/2005 | Belef et al. |
| 6,978,168 B2 | 12/2005 | Beatty et al. |
| 6,990,370 B1 | 1/2006 | Beatty et al. |
| 6,997,870 B2 | 2/2006 | Couvillon |
| 7,022,077 B2 | 4/2006 | Mourad et al. |
| 7,025,064 B2 | 4/2006 | Wang et al. |
| 7,027,892 B2 | 4/2006 | Wang et al. |
| 7,037,345 B2 | 5/2006 | Bottcher et al. |
| 7,076,300 B1 | 7/2006 | Kroll et al. |
| 7,189,208 B1 | 3/2007 | Beatty et al. |
| 7,344,533 B2 | 3/2008 | Pearson et al. |
| 7,466,303 B2 | 12/2008 | Yi et al. |
| 7,479,106 B2 | 1/2009 | Banik et al. |
| 7,632,265 B2 | 12/2009 | Hauck et al. |
| 7,806,829 B2 | 10/2010 | Hauck |
| 8,046,049 B2 * | 10/2011 | Govari et al. ............... 600/424 |
| 8,407,023 B2 * | 3/2013 | Hauck ............................ 702/95 |
| 8,755,864 B2 | 6/2014 | Hauck et al. |
| 2001/0027316 A1 | 10/2001 | Gregory |
| 2002/0042570 A1 | 4/2002 | Schaldach et al. |
| 2002/0045809 A1 | 4/2002 | Ben-Haim |
| 2002/0087166 A1 | 7/2002 | Brock et al. |
| 2002/0087169 A1 | 7/2002 | Brock et al. |
| 2002/0123749 A1 | 9/2002 | Jain |
| 2002/0128633 A1 | 9/2002 | Brock et al. |
| 2002/0143319 A1 | 10/2002 | Brock |
| 2002/0143326 A1 | 10/2002 | Foley et al. |
| 2002/0177789 A1 | 11/2002 | Ferry et al. |
| 2003/0036696 A1 | 2/2003 | Willis et al. |
| 2003/0055410 A1 | 3/2003 | Evans et al. |
| 2003/0199904 A1 | 10/2003 | Boecker et al. |
| 2004/0049205 A1 | 3/2004 | Lee et al. |
| 2004/0059237 A1 | 3/2004 | Narayan et al. |
| 2004/0073206 A1 | 4/2004 | Foley et al. |
| 2004/0098075 A1 | 5/2004 | Lee |
| 2004/0128026 A1 | 7/2004 | Harris et al. |
| 2004/0176751 A1 | 9/2004 | Weitzner et al. |
| 2004/0193146 A1 | 9/2004 | Lee et al. |
| 2004/0254437 A1 | 12/2004 | Hauck et al. |
| 2005/0004579 A1 | 1/2005 | Sneider et al. |
| 2005/0049580 A1 | 3/2005 | Brock et al. |
| 2005/0096643 A1 | 5/2005 | Brucker et al. |
| 2005/0102017 A1 | 5/2005 | Mattison |
| 2005/0137478 A1 | 6/2005 | Younge et al. |
| 2005/0192488 A1 | 9/2005 | Bryenton et al. |
| 2005/0197530 A1 | 9/2005 | Wallace et al. |
| 2005/0203382 A1 | 9/2005 | Govari et al. |
| 2005/0203394 A1 | 9/2005 | Hauck |
| 2005/0209589 A1 | 9/2005 | Berman et al. |
| 2005/0215983 A1 | 9/2005 | Brock |
| 2005/0216033 A1 | 9/2005 | Lee et al. |
| 2005/0222554 A1 | 10/2005 | Wallace et al. |
| 2005/0228440 A1 | 10/2005 | Brock et al. |
| 2005/0234437 A1 | 10/2005 | Baxter et al. |
| 2006/0004352 A1 | 1/2006 | Vaska et al. |
| 2006/0015096 A1 | 1/2006 | Kauck et al. |
| 2006/0025756 A1 | 2/2006 | Francischelli et al. |
| 2006/0052695 A1 | 3/2006 | Adam |
| 2006/0057560 A1 | 3/2006 | Hiavka et al. |
| 2006/0058692 A1 | 3/2006 | Beatty et al. |
| 2006/0084945 A1 | 4/2006 | Moll et al. |
| 2006/0084960 A1 | 4/2006 | Mester et al. |
| 2006/0095022 A1 | 5/2006 | Moll et al. |
| 2006/0098010 A1 | 5/2006 | Dwyer et al. |
| 2006/0100610 A1 | 5/2006 | Wallace et al. |
| 2006/0111692 A1 | 5/2006 | Moll et al. |
| 2006/0116575 A1 | 6/2006 | Willis |
| 2006/0149139 A1 | 7/2006 | Bonmassar et al. |
| 2006/0258935 A1 | 11/2006 | Pile-Spellman et al. |
| 2007/0021679 A1 | 1/2007 | Narayan et al. |
| 2007/0043296 A1 | 2/2007 | Schwartz |
| 2007/0057945 A1 | 3/2007 | Olson |
| 2007/0060833 A1 | 3/2007 | Hauck |
| 2007/0073179 A1 | 3/2007 | Afonso et al. |
| 2007/0185485 A1 | 8/2007 | Hauck et al. |
| 2007/0197896 A1 | 8/2007 | Moll et al. |
| 2007/0208260 A1 | 9/2007 | Afonso |
| 2008/0015670 A1 | 1/2008 | Pappone |
| 2009/0105579 A1 | 4/2009 | Garibaldi |

FOREIGN PATENT DOCUMENTS

| | | |
|---|---|---|
| WO | 0007501 | 2/2000 |
| WO | 0007503 | 2/2000 |
| WO | 0125822 | 4/2001 |
| WO | 2004047632 | 6/2004 |
| WO | 2005042053 | 5/2005 |
| WO | 2005044081 | 5/2005 |
| WO | 2005112750 | 12/2005 |
| WO | 2005117596 A2 | 12/2005 |
| WO | 2006059089 | 6/2006 |
| WO | 2007005976 | 1/2007 |

OTHER PUBLICATIONS

International Search Report for PCT/US07/080706 filed Oct. 8, 2007 and Written Opinion of International Search Authority dated Jun. 23, 2008.

International Search Report for PCT/US07/080698 filed Oct. 8, 2007 and Written Opinion of International Search Authority dated May 13, 2008.

International Search Report for PCT/US07/080705 filed Oct. 8, 2007 and Written Opinion of International Search Authority dated Apr. 16, 2008.

International Search Report for PCT/US07/080701 filed Oct. 8, 2007 and Written Opinion of International Search Authority dated Apr. 15, 2008.

International Search Report for PCT/US07/080703 filed Oct. 8, 2007 and Written Opinion of International Search Authority dated Apr. 16, 2008.

International Search Report for PCT/US07/080702 filed Oct. 8, 2007 and Written Opinion of International Search Authority dated Apr. 16, 2008.

* cited by examiner

ROBOTICALLY CONTROLLED CATHETER AND METHOD OF ITS CALIBRATION

CROSS-REFERENCE TO RELATED APPLICATIONS

This application is a continuation of U.S. application Ser. No. 13/441,249, filed 6 Apr. 2012 (the '249 application), now pending, which is a continuation of U.S. application Ser. No. 11/843,589, filed 22 Aug. 2007 (the '589 application), now U.S. Pat. No. 8,155,910, which is a continuation-in-part of U.S. application Ser. No. 11/139,908, filed 27 May 2005 (the '908 application), now U.S. Pat. No. 7,632,265. This application is also related to U.S. application Ser. No. 11/647,300, filed 29 Dec. 2006 (the '300 application), now pending, U.S. application Ser. No. 11/647,298, filed 29 Dec. 2006 (the '298 application), now pending, U.S. application Ser. No. 11/647,272, filed 29 Dec. 2006 (the '272 application), now pending, U.S. application Ser. No. 11/647,296, filed 29 Dec. 2006 (the '296 application), now pending, U.S. application Ser. No. 11/647,297, filed 29 Dec. 2006 (the '297 application), now pending, and U.S. application Ser. No. 11/647,304, filed 29 Dec. 2006 (the '304 application), now U.S. Pat. No. 7,974,674. The '249 application, the '589 application, the '908 application, the '300 application, the '298 application, the '272 application, the '296 application, the '297 application, and the '304 application are hereby incorporated by reference as though fully set forth herein.

BACKGROUND OF THE INVENTION a. Field of the Invention

The instant invention relates to robotically controlled devices employing positional feedback systems. In particular, the instant invention relates to a method for obtaining a transfer function in order to calibrate actuation of a robotically controlled device relative to the positional feedback system.

b. Background Art

Catheters are used for an ever growing number of medical procedures. To name just a few examples, catheters are used for diagnostic, therapeutic, and ablative procedures. Typically, the physician manipulates the catheter through the patient's vasculature to the intended site, such as a site within the patient's heart. The catheter typically carries one or more electrodes or other diagnostic or therapeutic devices, which may be used for ablation, diagnosis, cardiac mapping, or the like.

It is well known that, to facilitate manipulation of the catheter through the patient's vasculature to the intended site, portions of the catheter shaft, especially the distal regions thereof, may be made steerable. For example, the catheter may be manufactured such that the physician can translate, rotate, and deflect the distal end of the catheter as necessary and desired to negotiate the tortuous paths of the patient's vasculature en route to the target site.

By way of illustration, deflectability is oftentimes achieved by installing one or more steering wires (sometimes referred to as "pull wires") along the length of the catheter shaft. These steering wires are coupled to one or more actuators that the physician can utilize to selectively tension the wires, thereby deflecting the distal end of the catheter. It is also known that the pull wires may be coupled to a motorized, electromechanical control system for actuating the catheter on the deflection axis. Similarly, in order to advance and retract (that is, translate) the catheter, the catheter may be coupled to a motorized carriage.

Positional feedback systems (sometimes referred to as localization systems, navigation systems, or mapping systems, with the various terms being used interchangeably herein) may be used to provide the physician with information concerning the position or location of the catheter within the patient. U.S. Pat. No. 5,697,377 ("the '377 patent) and U.S. Pat. No. 5,983,126 ("the '126 patent"), both of which are hereby expressly incorporated by reference as if fully set forth herein, disclose navigation systems for determining the position or location of a catheter in a patient's heart.

In the systems of the '377 and '126 patents, current pulses are applied to pairs of orthogonally-arranged patch electrodes placed on the body of the patient. These patches are used to create electric fields inside the patient defining a set of orthogonal x, y, and z measurement axes. The patents teach small amplitude, low current pulses supplied continuously at three different frequencies, one on each axis. A location electrode placed within these electric fields—for example, within the patient's heart—experiences voltages depending on its location between the pairs of patch electrodes defining each axis. The voltage on the location electrode, when compared to that on a reference electrode, indicates the position of the location electrode relative to the reference electrode. Thus, the three voltages can be used to define a location of the location electrode, and thus the catheter, in three-dimensional space, which may be expressed as a rectangular (x, y, z) coordinate relative to a set of orthogonal measurement axes.

While the motors used to actuate a catheter are themselves quite precise, the mechanical systems employed to deflect, translate, or rotate the catheter are less so, especially where actuation forces must be transmitted over significant distances. In particular, the position of the catheter tip depends upon many variables, including the catheter's temperature, its recent movement history, and the tortuous path it is traversing, as well as the expected and desired dependence upon the displacement supplied to the pull wires or other mechanical and electromechanical system elements. Much of this variability is due to retained forces along the length of the catheter body and internal catheter structures, which may be collectively referred to as "memory." In fact, for a given displacement of the pull wires, these factors can result in a variation of the tip location in excess of 1 cm. Relative changes desired in tip position are not precisely predictable for the same reasons.

Furthermore, extant positional feedback systems, such as the navigation system described above, may have inherent error. Though intra-cardiac navigation systems are robust in terms of their reproducibility, the dimensional feedback that they provide tends to be contextual—dependent upon the particular patient, heart chamber structure, and other factors. Though this presents no difficulty for mapping applications, wherein all sites are mapped and marked in the same relative context, it does present a problem in open loop characterization of the catheter. For example, if the navigation system indicates that a 10 mm deflection is necessary, but this movement is, in reality, only 9 mm per the catheter's characteristics, an error of 1 mm results. This navigation system error is in addition to the device error discussed above.

Thus, it is desirable to obtain a transfer function relating the desired motion of the catheter in three-dimensional space to the control vectors or motion commands (referred to herein as "movement vectors") that are supplied to the motors. A first order calibration method might be to actuate the catheter for an expected movement and measure the actual movement utilizing the navigation system described above. A scale correction factor can be derived from the ratio of the expected movement to the actual movement. This approach, however, may account for some uncertainties of the catheter itself, but does not account for external error sources such as patient motion, cardiac motion, patient respiration, and electronic noise.

BRIEF SUMMARY OF THE INVENTION

Disclosed herein is a robotically controlled cardiac catheter and a method of calibrating the catheter. The calibration method establishes the relationship between the actuation supplied to the catheter and the actuation obtained while accounting for external error sources such as patient motion, cardiac motion, patient respiration, and electronic noise in the positional feedback system. This facilitates accurate and precise control of the robotically controlled catheter.

According to a first embodiment of the invention, a method of calibrating a robotic device capable of movement relative to at least one actuation axis generally includes: oscillating the robotic device on a first actuation axis by applying a first oscillation vector at a first oscillation frequency; while oscillating the robotic device on the first actuation axis, periodically measuring a location of the robotic device, thereby generating a first plurality of location data points measured as a function of time; processing the first plurality of location data points using a Fourier transform algorithm to isolate a displacement of the robotic device attributable to application of the first oscillation vector; and resolving an output of the processing step into a calibration vector for the first actuation axis. The location of the robotic device is measured for a sampling interval between about 0.5 seconds and about 10 seconds at a first sampling rate that is preferably a multiple of at least about two times greater than, and preferably between about five and about ten times greater than, the first oscillation frequency. The location of the robotic device may be measured relative to a plurality of measurement axes, thereby creating a first plurality of location data points for each of the measurement axes, which may then be independently processed using a Fourier transform algorithm. The calibration vector, in turn, may include at least one value for each of the measurement axes. The plurality of location data points may be stored in a buffer or other memory. The process may be repeated for any other actuation axes on which the robotic device may be actuated, with any or all of the oscillation frequencies, sampling intervals, and sampling rates optionally being equal for the actuation axes. Preferably, the actuation axes include a translation axis, a rotation axis, and a deflection axis.

According to another embodiment of the invention, a method of calibrating a robotically controlled catheter capable of movement relative to at least one actuation axis generally includes: mechanically actuating the catheter on a first actuation axis by applying a first oscillation vector at a first oscillation frequency; periodically measuring a location of the catheter, thereby generating a first plurality of location data points measured as a function of time; processing the first plurality of location data points using a Fourier transform algorithm to distinguish mechanical actuation of the catheter from at least one of patient motion, cardiac motion, respiration, and electronic noise; and resolving an output of the processing step into a calibration vector for the first actuation axis. The location of the catheter is measured for a sampling interval between about 0.5 seconds and about 10 seconds at a first sampling rate that is preferably a multiple of at least about two times greater than, and preferably between about five and about ten times greater than, the first oscillation frequency. The sampling rate is preferably between about 60 Hz and about 200 Hz, and more preferably is about 100 Hz, while the first oscillation frequency is preferably between about 1 Hz and about 10 Hz, and more preferably between about 3 Hz and about 5 Hz. The location of the catheter, for example, the location of the tip of the catheter, may be measured relative to a plurality of measurement axes, thereby creating a first plurality of location data points for each of the measurement axes, which may then be independently processed using a Fourier transform algorithm. The calibration vector, in turn, may include at least one value for each of the measurement axes. The plurality of location data points may be stored in a buffer or other memory. The process may be repeated for any other actuation axes on which the catheter may be actuated, with any or all of the oscillation frequencies, sampling intervals, and sampling rates optionally being equal for the actuation axes. Preferably, the actuation axes include a translation axis, a rotation axis, and a deflection axis.

In yet another embodiment of the invention, a method of calibrating a robotically controlled catheter generally includes: oscillating the catheter on an actuation axis by applying an oscillation vector at an oscillation frequency; periodically measuring a location of a point on the catheter, thereby generating a plurality of location data points measured as a function of time; applying a signal processing algorithm to the plurality of location data points to isolate a displacement of the catheter attributable to application of the oscillation vector; and resolving an output of the signal processing algorithm into a calibration vector for the actuation axis. The signal processing algorithm may be a Fourier transform algorithm. The plurality of data points is measured at a sampling rate that is preferably a multiple of and at least about two times greater than, and more preferably about five to about twenty times greater than, the oscillation frequency. The location of the catheter may be measured relative to one or more measurement axes, thereby creating a plurality of location data points for each of the measurement axes. The calibration vector, in turn, may include at least one component, including zero components, along each of the one or more measurement axes. The plurality of location data points may be stored in a buffer or other memory. The actuation axis is preferably selected from the group consisting of a translation axis, a deflection axis, and a rotation axis.

According to still another embodiment of the invention, a method of calibrating a robotically controlled catheter capable of movement relative to at least one actuation axis includes: mechanically actuating the catheter on a first actuation axis by applying a first oscillation vector at a first oscillation frequency; periodically measuring a location of the catheter to generate a first plurality of location data points measured as a function of time; and processing the first plurality of location data points using a Fourier transform algorithm to generate a transfer function that relates a position of the robotically controlled catheter to a movement vector for the first actuation axis. The process may be repeated for additional actuation axes.

In a further embodiment of the present invention, a robotically controlled medical device generally includes: an end-effector configured to perform a medical procedure; an actuator for moving the end-effector; a controller for mechanically actuating the end-effector by energizing the actuator to apply an oscillation vector on an actuation axis to the end effector; a positional feedback system for periodically measuring a location of the end-effector, thereby creating a plurality of location data points measured as a function of time; and a processor for processing the plurality of location data points according to a Fourier transform algorithm to generate a transfer function relating the position of the end-effector to a movement vector for the actuation axis. The end-effector may be a cardiac catheter. The positional feedback system may periodically measure a location of the end of the end-effector relative to one or more measurement axes, thereby creating a plurality of location data points for each of the one or more measurement axes, which may then be independently processed using a Fourier transform algorithm. The transfer function may comprise a calibration vector having at least one component, including zero components, directed along each of the one or more measurement axes.

A technical advantage of the present invention is that it accounts for device variability error, positional feedback system error, and external factor error in deriving a transfer function for calibrating a robotically controlled device.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
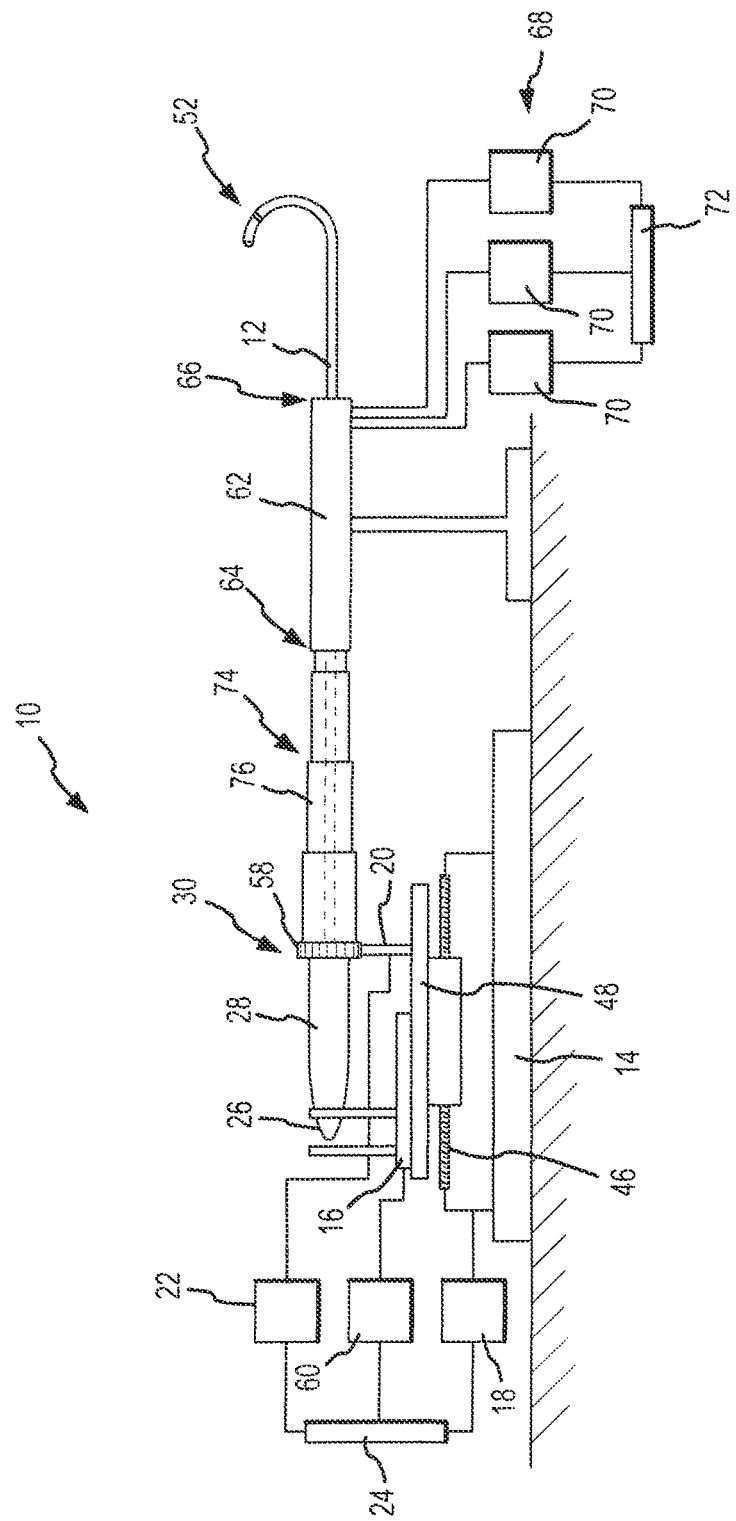
FIG. 1 is a schematic illustration of an embodiment of a robotic surgical system.

FIG. 1 schematically illustrates an embodiment of a robotic surgical system 10 for robotic manipulation and control of a medical device 12. Medical device 12 is preferably a catheter, which may be any type of catheter, including, by way of example only and without limitation, an ablation catheter, a guide wire catheter, an introducer catheter, a probe, or a stylet. It should be understood, however, that any other therapeutic, diagnostic, or assistive medical device may be controlled by robotic surgical system 10 without departing from the scope of the present invention. Such other devices include, but are not limited to, syringes, electrophoresis devices, iontophoresis devices, transdermal pharmaceutical delivery devices, myoblast delivery devices, stem cell delivery devices, ablation devices, stents, and pacemaker leads, which may be carried on or delivered by a catheter. It should further be understood that robotic surgical system 10 may be used to manipulate and control more than one medical device 12 in accordance with the quick installation and removal feature described herein. Accordingly, the terms "medical device," "probe," "therapeutic device," and "catheter" are used interchangeably herein. The general term "end effector" may also be used to describe medical device 12.

Robotic surgical system 10 generally includes a track 14, a catheter holding device 16, a translation servo mechanism 18, a catheter deflection control mechanism 20, a deflection servo mechanism 22, and a controller 24 operatively coupled to at least one of translation servo mechanism 18 and deflection servo mechanism 22. Translation and deflection servo mechanisms 18, 22 may be any type of device for providing mechanical control at a distance, including continuous motors, stepper motors, hydraulic actuators, pulley systems, and other devices known to those of ordinary skill in the art. Catheter deflection control mechanism 20 and deflection servo mechanism 22 are collectively referred to herein as a "catheter deflection mechanism."

Catheter holding device 16 includes a catheter receiving portion 26. Catheter receiving portion 26 is configured to receive catheter 12 by installing a catheter control handle 28, located near a proximal end 30 of catheter 12, into catheter receiving portion 26. Preferably, catheter receiving portion 26 is adapted for quick installation and removal of any type of catheter 12 (or, as noted above, another medical device), thereby facilitating the installation of device 12 for control by robotic surgical system 10 and removal of device 12 for manual control (e.g., user manipulation of catheter control handle 28). Accordingly, catheter control handle 28 may be secured in catheter receiving portion 26 by a frictional fit or with one or more quick-release fasteners. Alternatively, the inner surface of catheter receiving portion 26 and the outer surface of catheter control handle 28 may include mating threaded portions to permit catheter control handle 28 to be screwed into catheter holding device 16. In other embodiments of robotic surgical system 10, catheter control handle 28 is clamped or strapped in place in catheter receiving portion 26. An adapter may also be used to facilitate the reception of catheter control handle 28 within catheter receiving portion 26.

Figure 2:
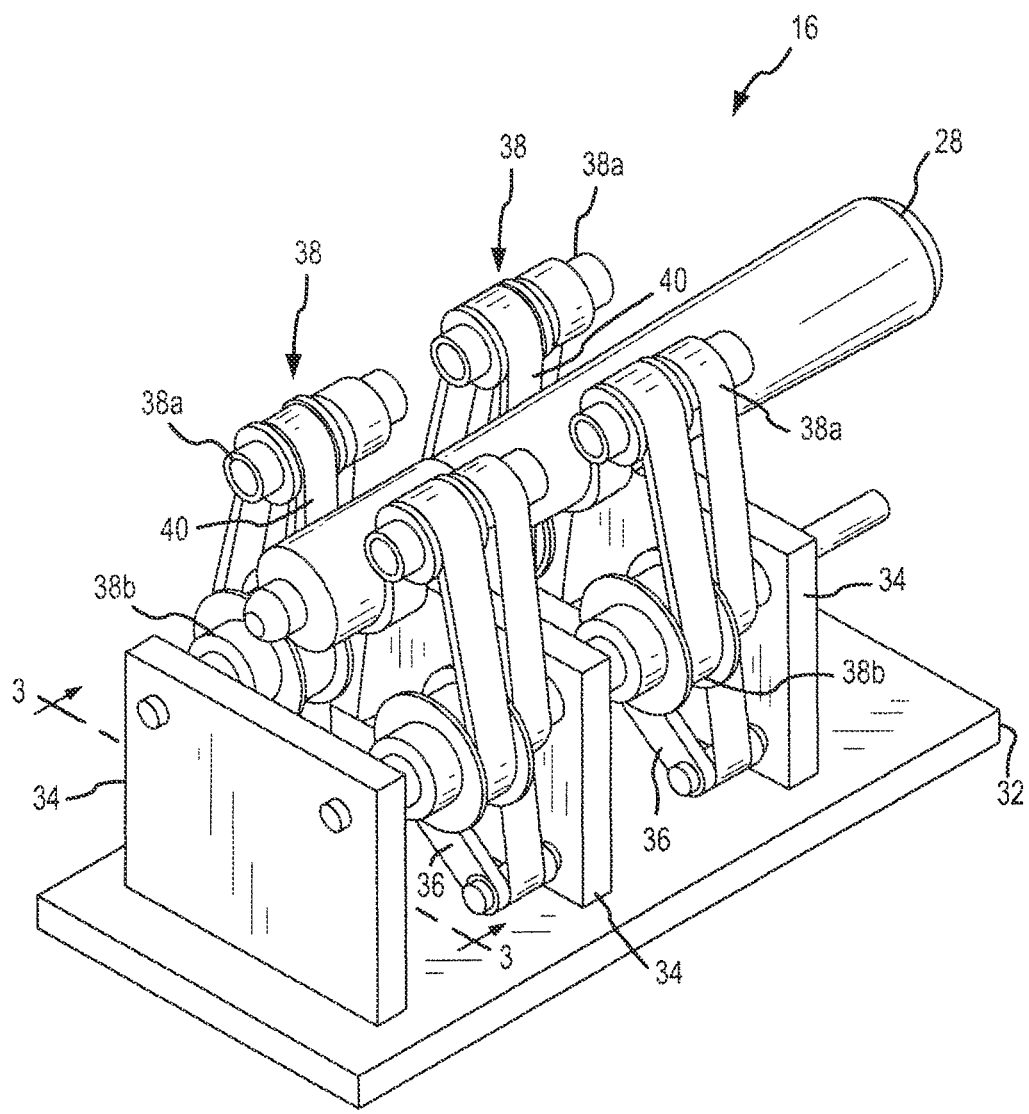
FIG. 2 is a perspective view of one embodiment of a catheter holding device with a catheter placed therein.
Figure 3:
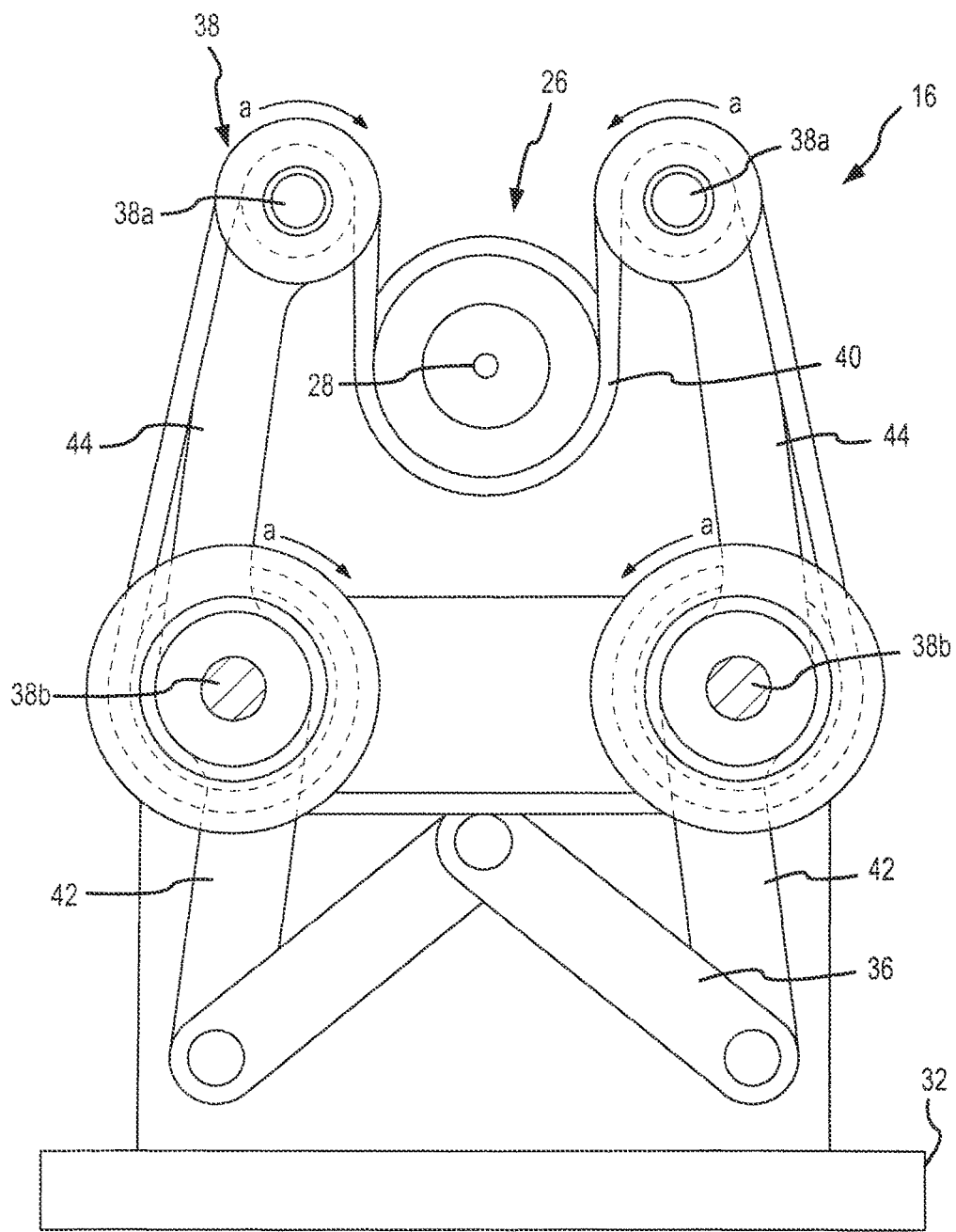
FIG. 3 is an end view of the catheter holding device of FIG. 2.

One embodiment of catheter holding device 16 is illustrated in FIGS. 2 and 3 with catheter control handle 28 placed, but not secured, therein. Catheter holding device 16 includes a base plate 32 and a plurality of upstanding support plates 34. Support plates 34 support cams 36, which are connected to pulley systems 38.

Figure 4:
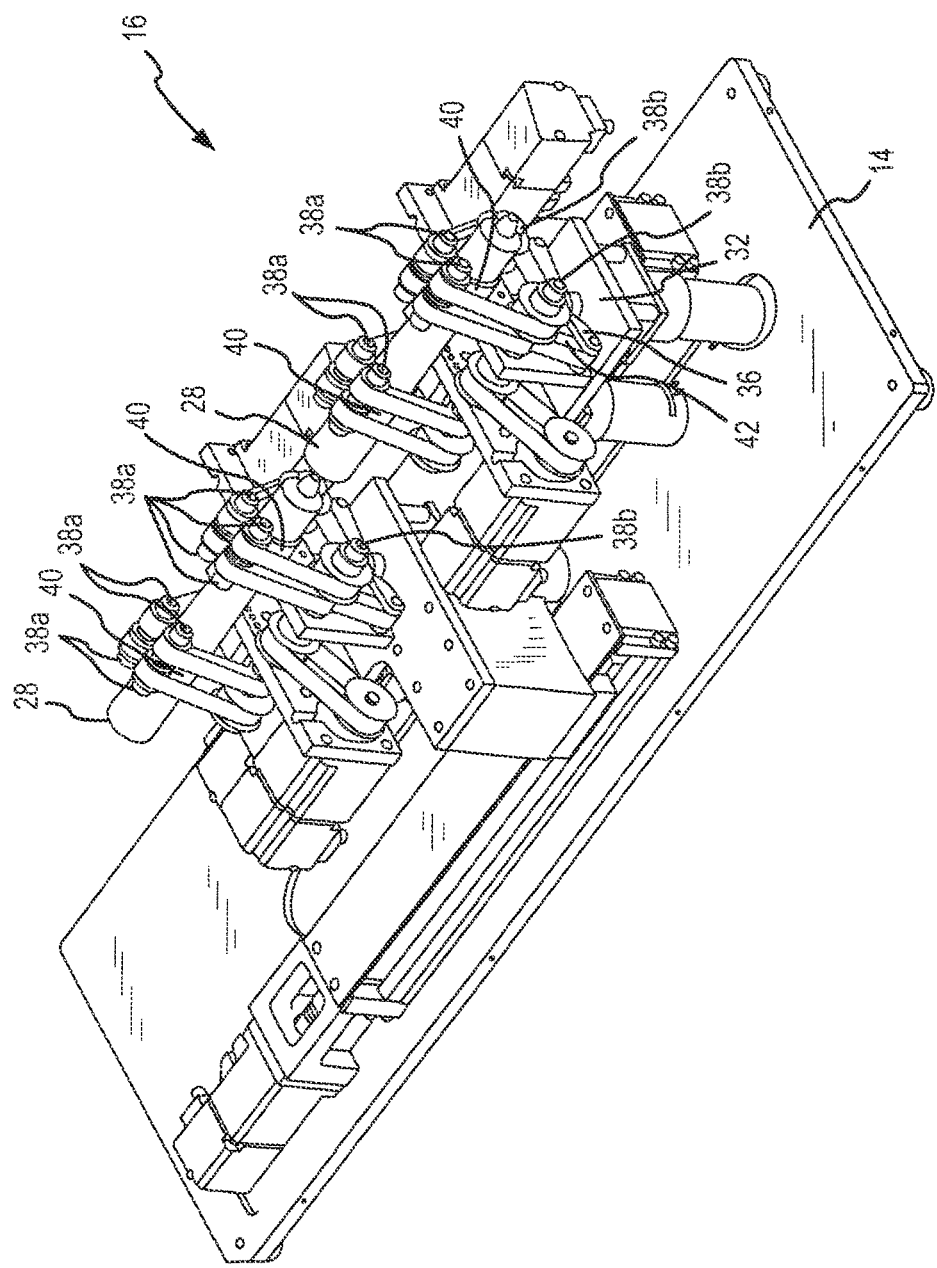
FIG. 4 is a perspective view of one embodiment of a catheter holding device with a catheter secured therein.
Figure 5:
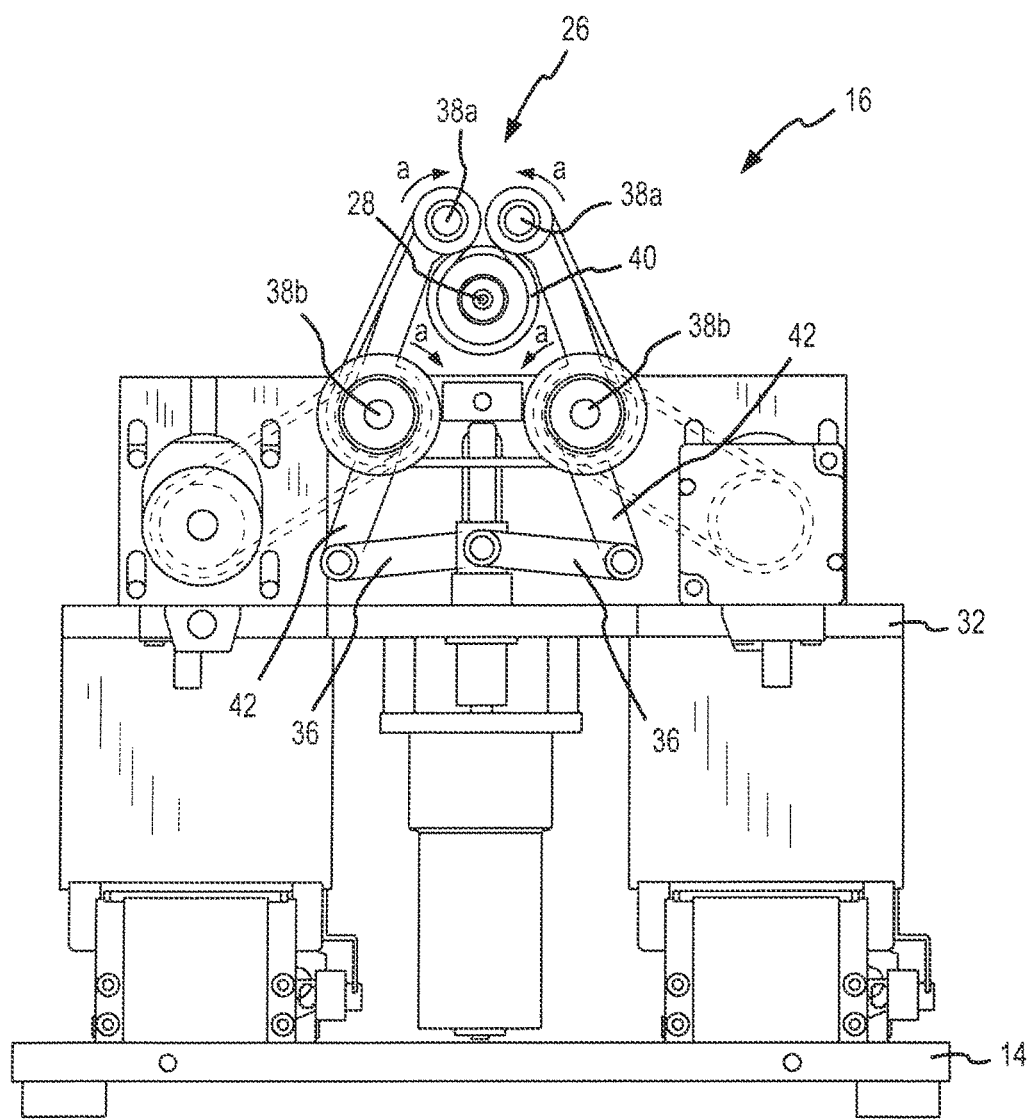
FIG. 5 is an end view of the catheter holding device of FIG. 4.

Catheter control handle 28 is received downwardly through an opening 40 into the catheter receiving portion 26 and onto belts 40 of pulley systems 38. As catheter control handle is urged downwardly, belts 40 rotate upper and lower pulleys 38a, 38b in the direction of arrows a. This, in turn, urges cams 36 downwards via links 42 and draws upper pulleys 38a, 38b towards one another via links 44, while simultaneously wrapping the belts 40 about catheter control handle 28. Catheter control handle 28 is thereby secured within catheter receiving portion 26 as shown in FIGS. 4 and 5. To remove catheter control handle 28 from catheter holding device 16, the user need only release cams 26, which reverses the process described above and opens catheter receiving portion 26.

Catheter holding device 16 is translatably associated with track 14. The phrase "translatably associated with" encompasses all types of relative lateral motion between catheter holding device 16 and track 14. For example, catheter holding device 16 may slide relative to track 14. Alternatively, catheter holding device 16 may move laterally along a screw mechanism 46, such as a worm gear, a lead screw, or a ball screw, attached to track 14. Preferably, catheter holding device 16 has a translation range relative to track 14 (i.e., the lateral distance that catheter holding device 16 can travel relative to track 14 between extremes) of at least about 5 cm, the approximate width of a human heart. More preferably, the translation range of catheter holding device 16 relative to track 14 is at least about 10 cm.

In the preferred embodiment of the invention, a carriage 48 is translatably mounted on track 14 via screw mechanism 46. Catheter holding device 16 is mounted on carriage 48 such that catheter holding device 16 translates relative to track 14 with carriage 48. For example, base plate 32 may be fixedly or removably mounted on carriage 48. Alternatively, catheter holding device 16 may be integrally formed with carriage 48 as a single assembly (i.e., base plate 32 and carriage 48 may be a single, unitary component). Likewise, in some embodiments of the invention, catheter holding device 16 may be translatably mounted directly on track 14 without an intervening carriage.

Translation servo mechanism 18 is operatively coupled to catheter holding device 16 and adapted to control translation of catheter holding device 16 relative to track 14 in order to adjust the lateral position of catheter holding device 16 along track 14. Preferably, translation servo mechanism 18 is operatively coupled to carriage 48 in order to move carriage 48, and therefore catheter holding device 16 mounted thereon, laterally along track 14. In the embodiment shown in FIG. 1, translation servo mechanism 18 drives screw mechanism 46, thereby moving carriage 48 laterally therealong.

Deflection servo mechanism 22 is operatively coupled to and adapted to control catheter deflection control mechanism 20. In the preferred embodiment of the invention, deflection servo mechanism 22 is operatively coupled to catheter deflection control mechanism 20 such that deflection servo mechanism 22 can rotate catheter deflection control mechanism 20. Either or both of deflection servo mechanism 22 and catheter deflection control mechanism 20 may be mounted on carriage 48 in order to simplify the transmission system linking deflection servo mechanism 22 and catheter deflection control mechanism 20. In some embodiments of robotic surgical system 10, catheter deflection control mechanism 20 is incorporated in catheter holding device 16, for example by utilizing pulley systems 38, and in particular belts 40, as further described below. One of ordinary skill in the art will appreciate, however, that catheter deflection control mechanism 20 may also be separated from catheter holding device 16 without departing from the spirit and scope of the present invention.

Controller 24 is adapted to control at least one of translation servo mechanism 18 and deflection servo mechanism 22 in order to navigate catheter 12 received in catheter holding device 16. It should also be noted that the use of multiple controllers to control translation servo mechanism 18 and deflection servo mechanism 22 is regarded as within the scope of the present invention. Throughout this disclosure, the term "controller" refers to a device that controls the movement or actuation of one or more robotic systems (that is, the component responsible for providing command inputs to the servo mechanisms). One of ordinary skill in the art will understand how to select an appropriate controller for any particular mechanism within robotic surgical system 10. Further, the term "controller" should be regarded as encompassing both a singular, integrated controller and a plurality of controllers for actuating one or more robotic systems.

Figure 6:
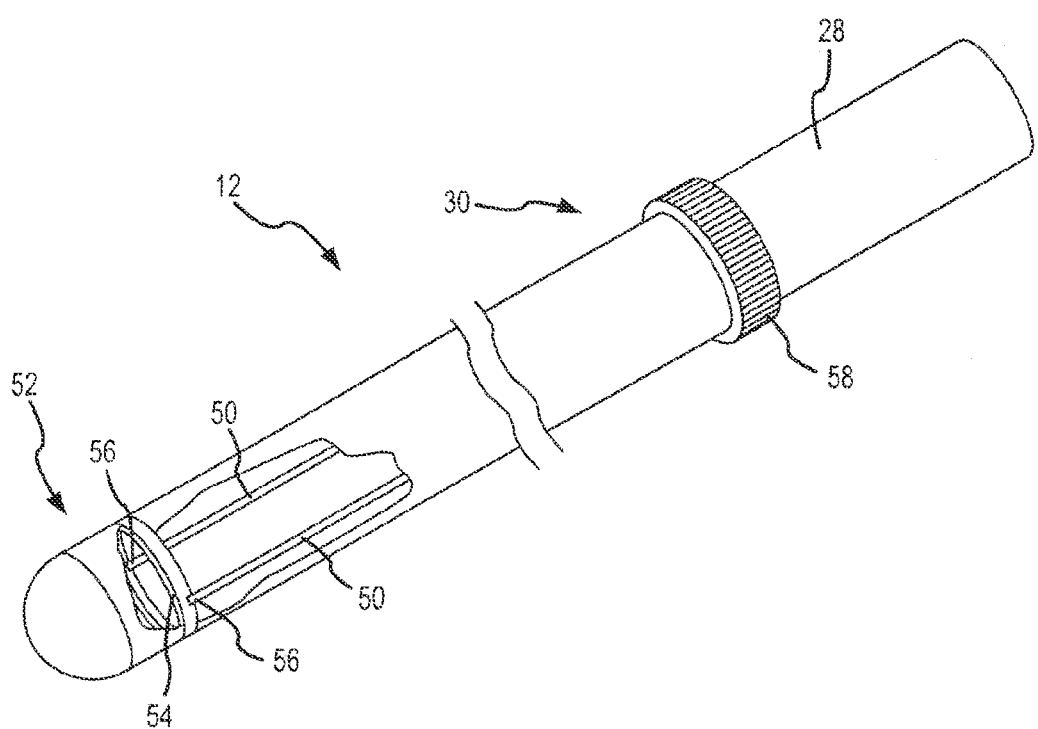
FIG. 6 illustrates an exemplary steerable catheter such as may be used in the robotic surgical system.

As shown in FIG. 6, catheter 12 is preferably a steerable catheter including at least one pull wire 50 extending from catheter control handle 28 near proximal end 30 of catheter 12 to a distal end 52 of catheter 12. Pull wires 50 may be coupled to at least one pull ring 54, also located near distal end 52 of catheter 12. When placed in tension, pull wires 50 deflect distal end 52 of catheter 12 into various configurations. As one of skill in the art will understand, additional pull wires 50 will enhance the deflection versatility of distal end 52 of catheter 12. For example, a single pull wire 50 with a single point of attachment to pull ring 54 will permit distal end 52 of catheter 12 to deflect on a single axis, and perhaps in only one direction, for example upwards relative to FIG. 6. By adding a second pull wire 50 (as shown in FIG. 6), or by looping a single pull wire 50 to have two points of attachment 56 to pull ring 54, distal end 52 of catheter 12 may be deflected in two directions, for example both upwards and downwards relative to FIG. 6. A catheter 12 with four pull wires 50 attached to pull ring 54 at about 90° intervals can deflect in four directions, for example upwards, downwards, and into and out of the plane of the paper relative to FIG. 6.

One or more catheter deflection actuators 58 may be provided on catheter control handle 28 to selectively tension one or more pull wires 50, thereby controlling the direction and degree of deflection of distal end 52 of catheter 12. In some embodiments, one or more knobs may be provided, rotation of which selectively tension one or more pull wires 50. It should be understood, however, that catheter deflection actuators 58 may take many other forms, including, but not limited to, sliders and switches, without departing from the spirit and scope of the present invention. Additionally, it is contemplated that rotating catheter control handle 28 itself may selectively tension pull wires 50 and deflect distal end 52 of catheter 12.

Returning to FIG. 1, when catheter control handle 28 is received within catheter receiving portion 26, catheter 12 translates relative to track 14 with catheter holding device 16, thereby providing a first degree of freedom permitting catheter 12 to be advanced into and retracted from a patient's body. Additionally, catheter 12 is operatively coupled to catheter deflection control mechanism 20 such that actuation of catheter deflection control mechanism 20 causes distal end 52 of catheter 12 to deflect, thereby providing a second degree of freedom to catheter 12. In particular, catheter deflection actuator 58 may be operatively coupled to catheter deflection control mechanism 20 such that catheter deflection control mechanism 20 can actuate catheter deflection actuator 58 to selectively tension one or more pull wires 50 and deflect the distal end 52 of catheter 12 by a desired amount in a desired direction.

In some embodiments of the invention, rotating catheter deflection control mechanism 20 will rotate catheter deflection actuator 58 in turn, thereby selectively tensioning one or more pull wires 50 within catheter 12. The transmission system between catheter deflection control mechanism 20 and catheter deflection actuator 58 may be a frictional fit provided, for example, by rubberized coatings surrounding catheter deflection control mechanism 20 and catheter deflection actuator 58. Alternatively, catheter deflection control mechanism 20 and catheter deflection actuator 58 may be coupled with mating gear teeth or knurling.

Referring specifically to the embodiment of catheter holding device 16 depicted in FIGS. 2-5, when catheter 12 is secured in catheter receiving portion 26, belts 40 frictionally engage catheter control handle 28. They may also engage catheter deflection actuator 58. Thus, if pulley system 38 is driven by deflection servo mechanism 22, belts 40 may rotate catheter control handle 28, catheter deflection actuator 58, or both, in order to selectively tension one or more pull wires 50 and deflect distal end 52 of catheter 12.

It should be understood that the particular configurations of catheter deflection control mechanism 20 and catheter deflection actuator 58 described above are merely exemplary and can be modified without departing from the spirit and scope of the invention. For example, if catheter deflection actuator 58 is a slider rather than a knob, catheter deflection control mechanism 20 may be suitably modified, or even replaced as a modular unit, to actuate a slider. This facilitates the quick connect/disconnect operation of robotic surgical system 10 by allowing easy installation and interconnection between off-the-shelf medical devices of varying construction and robotic surgical system 10.

As described above, the inclusion of additional pull wires 50 in catheter 12 increases the number of directions in which distal end 52 of catheter 12 can deflect. This is referred to herein as "deflection versatility." Where relatively few pull wires 50 (e.g., fewer than about four pull wires 50) are used, however, compensation for lost deflection versatility may be had by rotating catheter 12 about its axis. For example, in a catheter using only a single pull wire 50 with a single point of attachment to pull ring 54, permitting the catheter to deflect only in one direction, the catheter may be deflected in the opposite direction simply by rotating it 180° about its axis. Similarly, a catheter that can deflect in two directions 180° apart can be deflected in the directions midway therebetween by rotating the catheter 90° about its axis.

Accordingly, in some embodiments of the invention, catheter receiving portion 26 is rotatable. An example of such a rotatable catheter receiving portion is catheter receiving portion 26 defined by pulley system 38 depicted in FIGS. 2-5. A rotation servo mechanism 60 is operatively coupled to rotatable catheter receiving portion 26 and adapted to control rotatable catheter receiving portion 26. Thus, pulley system 38 may be driven by rotation servo mechanism 60, thereby engaging belts 40 to rotate catheter 12 about its axis.

If desired, rotation servo mechanism 60 may be mounted on carriage 48 or affixed to catheter holding device 16 such that rotation servo mechanism 60 translates relative to track 14 with catheter holding device 16. This arrangement creates a fixed-distance relationship between rotation servo mechanism 60 and catheter holding device 16, which can simplify the transmission system coupling rotation servo mechanism 60 to catheter holding device 16.

When installed in catheter holding device 16, catheter 12 rotates with catheter receiving portion 26, thereby providing a third degree of freedom to catheter 12 and compensating for low deflection versatility attributable to a relatively lower number of pull wires 50. Catheter receiving portion 26 is preferably rotatable at least about 360° about its axis, such that catheter 12 received therein is also rotatable at least about 360° about its axis, thereby facilitating deflection of distal end 52 of catheter 12 in substantially any direction, significantly enhancing the deflection versatility of the distal end 52 of the catheter 12. Catheter receiving portion 26 may also be designed to rotate about 720° or more about its axis.

Rotating catheter 12 by rotating catheter receiving portion 26 may cause inadvertent deflection of distal end 52 of catheter 12. As one skilled in the art will recognize from this disclosure, as catheter receiving portion 26 and catheter 12 rotate, catheter deflection actuator 58 may remain stationary, rather than rotating with catheter control handle 28, if the torque applied by rotation servo mechanism 60 is insufficient to overcome the inertia of catheter deflection control mechanism 20. That is, catheter deflection actuator 58 may bind against catheter deflection control mechanism 20, causing relative rotation between catheter control handle 28 and catheter deflection actuator 58. This relative rotation may result in uncommanded tensioning of one or more pull wires 50, inadvertently deflecting distal end 52 of catheter 12.

To maintain a substantially constant deflection as catheter 12 rotates, therefore, controller 24 may be operatively coupled to both rotation servo mechanism 60 and deflection servo mechanism 22. Controller 24 is adapted to control at least one of deflection servo mechanism 22 and rotation servo mechanism 60, and preferably to simultaneously control both deflection servo mechanism 22 and rotation servo mechanism 60, to maintain a substantially constant deflection of distal end 52 as catheter receiving portion 26 and catheter 12 rotate. For example, as controller 24 commands rotation servo mechanism 60 to rotate catheter receiving portion 26, controller 24 may simultaneously command deflection servo mechanism 22 to actuate catheter deflection control mechanism 20 to counter-rotate, thereby substantially eliminating relative rotation between the catheter deflection actuator 58 and catheter control handle 28, helping to maintain a substantially constant deflection of catheter 12. Alternatively, as controller 24 commands rotation servo mechanism 60 to rotate catheter receiving portion 26, it may simultaneously command deflection servo mechanism 22 to decouple catheter deflection control mechanism 20 from catheter deflection actuator 58, thereby permitting catheter deflection actuator 58 to rotate freely with catheter control handle 28. In either case, controller 24 may be configured to eliminate the need to couple deflection servo mechanism 22 and rotation servo mechanism 60 through a mechanical transmission system such as a differential. Further, though described herein as a single controller adapted to control the translation, deflection, and rotation servo mechanisms 18, 22, 60, multiple controllers may be used without departing from the spirit and scope of the present invention.

An introducer 62, preferably a steerable introducer, and most preferably an Agilis™ steerable introducer, may be provided as part of robotic surgical system 10. A proximal end 64 of introducer 62 is preferably stationary, while a distal end 66 of introducer 62 extends into a patient (not shown for clarity) to a location proximate a target site (the term "target" is used herein to refer to a location at which treatment or diagnosis occurs). Introducer 62 may be steerable via a robotic control system 68 including at least one servo mechanism 70 adapted to control distal end 66 of introducer 62 in at least one degree of freedom. Preferably, robotic control system 68 includes three servo mechanisms 70 adapted to control distal end 66 of the introducer 62 in three degrees of freedom (translation, deflection, and rotation), resulting in a total of six degrees of freedom for robotic surgical system 10, and at least one controller 72 adapted to control servo mechanisms 70. Similar control principles may be applied to steerable introducer 62 as are described herein with respect to robotic surgical system 10 and medical device 12.

To create a substantially sterile field around catheter 12 outside the patient's body, an expandable and collapsible tubular shaft 74 substantially surrounds at least a portion of catheter 12, such as the region of catheter 12 between catheter holding device 16 and proximal end 64 of introducer 62. Preferably, shaft 74 is sterilized before use along with other relevant components of robotic surgical system 10. As catheter holding device 16 translates to advance catheter 12 into the patient (i.e., to the right in FIG. 1), tubular shaft 74 collapses upon itself. Contrarily, as catheter holding device 16 translates to retract catheter 12 from the patient (i.e., to the left in FIG. 1), tubular shaft 74 expands. Preferably, tubular shaft 74 is assembled from a plurality of telescoping tubular elements 76. It is contemplated, however, that tubular shaft 74 may alternatively be an accordion-pleated or other expandable and collapsible structure.

Robotic surgical system 10 may be employed to robotically navigate catheter 12 into and through the patient and to one or more sites within the patient's body by actuating one or more of translation servo mechanism 18, deflection servo mechanism 22, and rotation servo mechanism 60 (if present) via controller 24. Robotic surgical system 10 may operate automatically according to a computerized program as executed by controller 24. It is also contemplated that the user, who may be a surgeon, cardiologist, or other physician, may control robotic surgical system 10 through an appropriate set of controls, such as a three-dimensional joystick (e.g., a joystick with three input axes), a steering yoke, or another suitable input device or collection of such devices permitting the user to robotically steer catheter 12.

One of ordinary skill in the art will appreciate the desirability of knowing the relationship between the movement vector inputs at servo mechanisms 18, 22, 60 to the movement of catheter 12. A method and system of establishing this relationship will be described with reference to FIGS. 7 and 8.

Figure 7:
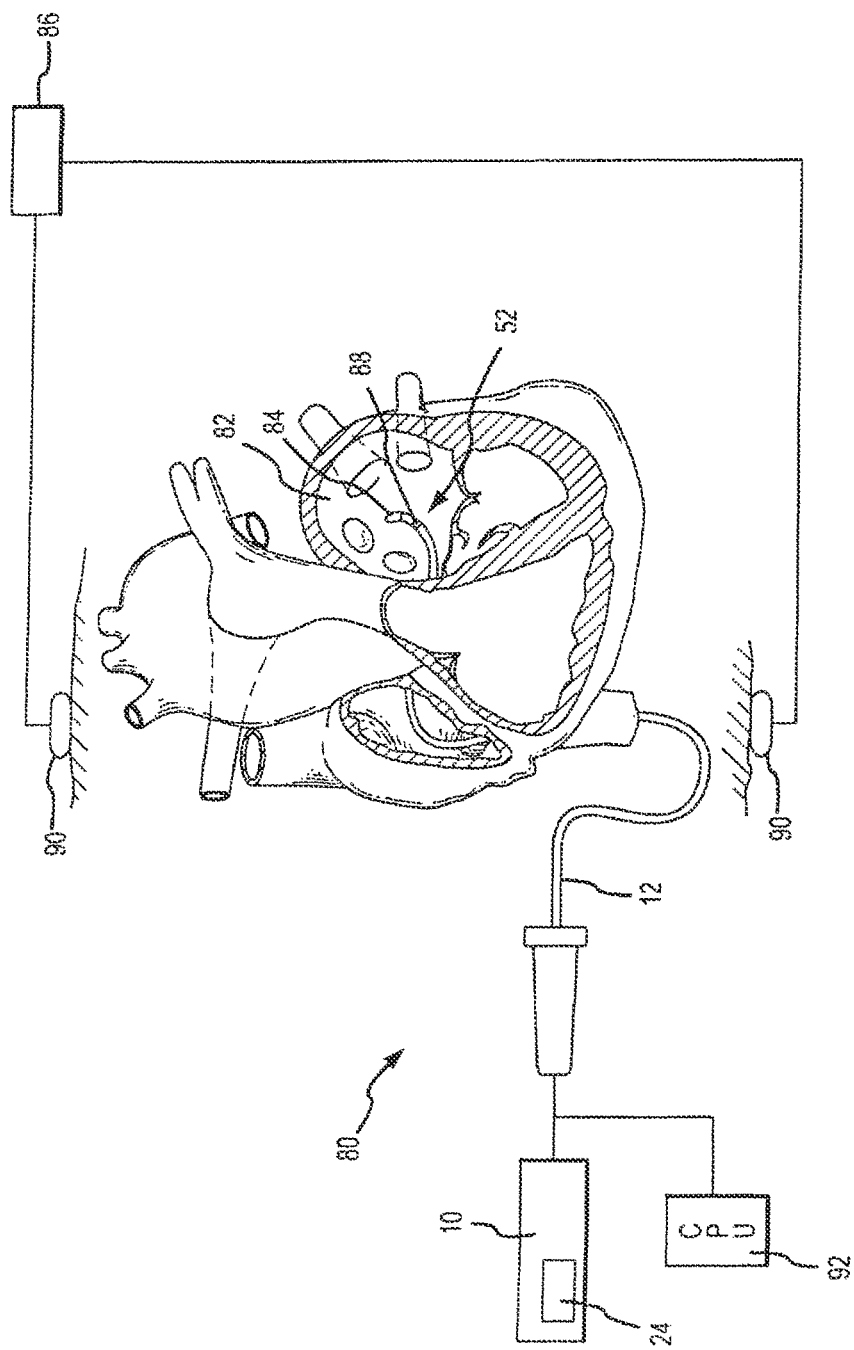
FIG. 7 schematically illustrates a robotic surgical system and a localization system such as may be used in the present invention.

FIG. 7 schematically illustrates a surgical system 80 including catheter 12 that is robotically controlled via robotic surgical system 10 as commanded by controller 24. Inputs to robotic surgical system 10 may be provided through computer system 92.

For purposes of illustration, catheter 12 is shown inserted into a chamber 52 of a patient's heart 82. Catheter 12 carries one or more sensors or electrodes 84, 88 thereon to locate catheter 12 using a positional feedback system 86. Preferably, positional feedback system 86 is the Ensite NavX™ system of St. Jude Medical, Inc., which includes pairs of electrodes 90 defining measurement axes by which the position of catheter 12 may be measured. For illustration purposes, only a single pair of electrodes 90 is shown. It is anticipated that other localization systems, including, for example, the CARTO navigation system from Biosense Webster, Inc., may also be employed.

Controller 24 may be commanded to mechanically actuate catheter 12 by energizing an actuator, such as one or more of servo mechanisms 18, 22, 60, to apply an oscillation vector on an actuation axis to catheter 12. While catheter 12 is being oscillated, positional feedback system 86 periodically measures a location of catheter 12, thereby creating a plurality of location data points that are measured as a function of time. As described above, the plurality of location data points may be measured relative to one or more measurement axes to create a plurality of location data points for each of the one or more axes.

Computer system 92 further includes a processor for processing the plurality of location data points according to a signal processing algorithm, such as a Fourier transform algorithm, to generate a transfer function relating a position of catheter 12 to a movement vector for the actuation axis (e.g., an input a servo mechanism such as servo mechanism 18, 22, or 60). The signal processing algorithm may be applied separate and independently to the plurality of location data points for each of the one or more measurement axes. The transfer function may comprise a calibration vector including at least one component directed along each of the one or more measurement axes.

Figure 8:
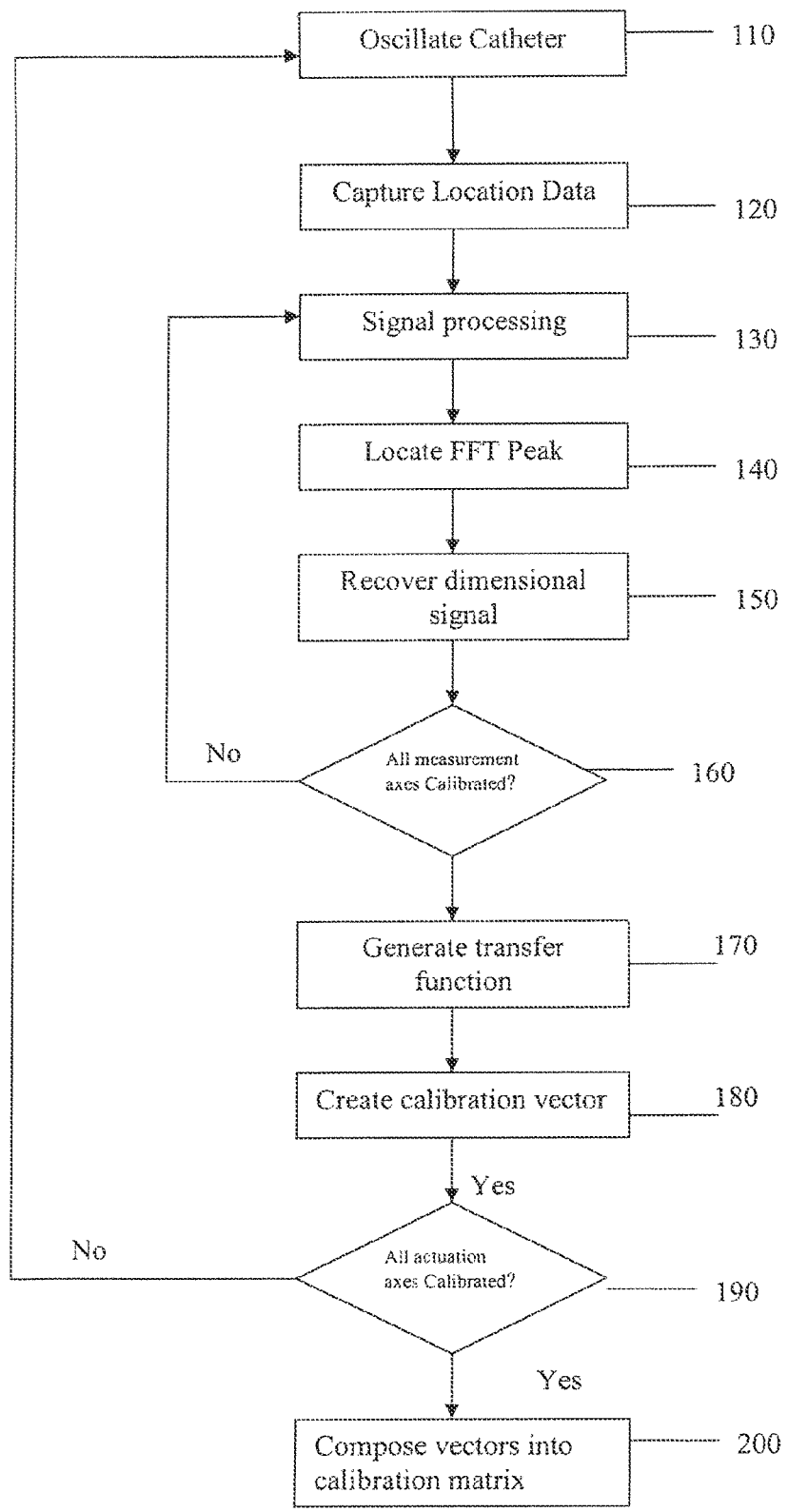
FIG. 8 is a flowchart of a method of calibrating a robotically controlled cardiac catheter or other robotically controlled device.

A method of calibrating catheter 12 on its actuation axes is illustrated in the flowchart of FIG. 8. In step 110, a first oscillation vector is applied to catheter 12 at a first oscillation frequency. The first oscillation vector mechanically actuates catheter 12 on a first actuation axis, for example the translation axis, causing oscillation of catheter 12 thereon. Preferably, the first oscillation vector actuates catheter 12 on only the first actuation axis such that the resultant actual oscillation of catheter 12 is limited to the first actuation axis. Thus, application of the first oscillation vector may require inputs to one or more of servo mechanisms 18, 22, 60. For example, as described above, actuating catheter 12 on only the rotation axis may require inputs to both deflection servo mechanism 22 and rotation servo mechanism 60.

As one skilled in the art will appreciate, various error sources may introduce apparent oscillations on other actuation axes (that is, due to error sources, it may appear that, when actuated on the first actuation axis, catheter 12 is also moving on one or more of the remaining actuation axes). As discussed herein, it is an object of this invention to isolate the actual mechanical oscillation of catheter 12 on the first actuation axis from the apparent oscillations of catheter 12 attributable to these error sources.

The first oscillation vector is preferably a small motion vector resulting in an expected oscillation on the first actuation axis of between about 1 mm and about 10 mm, and more preferably between about 2 mm and about 3 mm. While larger distances are contemplated, a short distance is often sufficient to permit the actuator to be accurately characterized. The first oscillation frequency is preferably between about 1 Hz and about 10 Hz, and more preferably between about 3 Hz and about 5 Hz.

In step 120, a location of catheter 12 (or a point thereon) is periodically measured. The location measured may be that of the tip of catheter 12 (e.g., electrode 84). This creates a first plurality of location data points that are measured as a function of time. In some embodiments of the invention, the location of catheter 12 is measured relative to a plurality of measurement axes, which may differ from the actuation axes. For example, the location of catheter 12 may be measured relative to the x-axis, y-axis, and z-axis of the navigation system disclosed in the '377 and '126 patents, described above, or relative to the axes defined by patch electrodes 90 illustrated in FIG. 7. Thus, step 120 creates a plurality of location data points as a function of time for each of the measurement axes (for example, a plurality of (x, y, z) coordinate points, or, alternatively separate pluralities of location data points for each of the measurement axes).

Measuring step 120 occurs for a period of time (referred to herein as the "sampling interval") between about 0.5 seconds and about 10 seconds, and preferably of about 3 seconds, occurring simultaneously with oscillating step 110 (that is, the location of catheter 12 is periodically measured while catheter 12 is being oscillated on the first actuation axis). The first plurality of location data points may optionally be stored in a buffer or other memory, which may be part of computer system 92. Where the location of catheter 12 is measured relative to a plurality of measurement axes, the plurality of location data points for each of the measurement axes may be stored separately (e.g., a first plurality of location data points for the x-axis, a first plurality of location data points for the y-axis, and a first plurality of location data points for the z-axis). It is also contemplated that the plurality of location data points for each of the measurement axes may be stored collectively, for example as a first plurality of (x, y, z) coordinates.

During the sampling interval, the first plurality of location data points are measured at a first sampling rate, which is preferably a multiple of the first oscillation frequency at least two times greater than the first oscillation frequency, and is more preferably between about five times greater and about twenty times greater than the first oscillation frequency. Most preferably, the first sampling rate is between about 60 Hz and about 200 Hz, with a first sampling rate of about 100 Hz being particularly preferred. Setting the first sampling rate as a multiple of the first oscillation frequency ensures that an integral number of oscillations will be captured during the sampling interval.

As one skilled in the art will recognize from this disclosure, and as briefly mentioned above, the first plurality of location data points generated in step 120 reflects both the mechanical actuation of catheter 12 and any error sources. These error sources include, but are not limited to, catheter memory, patient motion, cardiac motion (e.g., the beating of the heart), respiration, friction, and electronic noise. In subsequent steps, the actual displacement of catheter 12 attributable to application of the first oscillation vector in step 110 is isolated, thereby distinguishing mechanical actuation of catheter 12 attributable to the first oscillation vector from apparent oscillations attributable to one or more error sources.

Accordingly, the first plurality of location data points is processed using a signal processing algorithm in step 130. The signal processing algorithm is preferably a Fourier transform algorithm, though other signal processing algorithms may be employed without departing from the spirit and scope of the present invention. Other suitable signal processing algorithms include, but are not limited to, synchronous demodulation or cross correlation, wherein waveforms that are facsimiles of the mechanical forcing function (e.g., the oscillation vector) are multiplied by the measured navigation signal (e.g., the plurality of location data points) obtained from each navigation (e.g., measurement) axis. This advantageously permits the relative displacement on each navigation axis to be extracted from motion and noise not related to the mechanical forcing function (that is, it permits isolation of mechanical actuation of catheter 12 attributable to the first oscillation vector from apparent oscillations attributable to one or more error sources or other influences).

When the location of catheter 12 is measured relative to a plurality of measurement axes, resulting in the generation of a plurality of location data points for each of the measurement axes, processing step 130 may include separately processing the plurality of location data points for each of the measurement axes using a signal processing algorithm such as a Fourier transform algorithm, though the plurality of location data points for each of the measurement axes could be collectively processed (e.g., applying a signal processing algorithm to the plurality of (x, y, z) coordinate points) without departing from the spirit or scope of the present invention.

As mentioned above, the sampling interval captures an integral number of oscillations of catheter 12 on the first actuation axis. By enforcing the integral relation between the forcing function frequency and the sampling interval, the Fourier power spectrum algorithm will typically produce a single peak at the first oscillation frequency in step 140, as opposed to a peak spread over more than one frequency bin. The value from the frequency bin corresponding to the forcing function may then simply be scaled to recover a dimensionally relevant signal in step 150. This signal processing effectively isolates movement of catheter 12 attributable to the application of the first oscillation vector, and may be independently repeated for each of the measurement axes, as shown in decision block 160. It is also contemplated, however, that the first plurality of location data points may be processed without resolution into measurement axis components.

In step 170, a transfer function relating a position of catheter 12 to a movement vector for the first actuation axis is generated from the dimensional signal or signals recovered during signal processing. The transfer function calibrates catheter 12 on the first actuation axis by establishing the correlation between the desired or expected movement of catheter 12 and the movement vector commands input thereto (e.g., the inputs to one or more of servo mechanisms 18, 22, and 60), thereby ensuring accurate execution of actuation commands and permitting precise control of catheter 12 along at least the first actuation axis.

The transfer function generated in step 170 may be resolved into a calibration vector for the first actuation axis in step 180. The calibration vector may include at least one value for each of the measurement axes—in other words, the calibration vector may include at least one component directed along each of the measurement axes expressing the vector difference between the applied oscillation vector and the actual measured response of catheter 12. It should be understood that one or more of these vector components may be a zero component in the event that catheter 12 is aligned as expected relative to a particular measurement axis on the first actuation axis. As described above, the calibration vector relates the desired or expected movement of catheter 12 to the actual movement of catheter 12, thereby defining the relationship between the inputs provided to catheter 12 (e.g., translation commands sent to translation servo mechanism 18) and their real-world outputs (e.g., translations of distal end 52 of catheter 12).

As shown at step 190, the process described in detail above may be repeated for any remaining actuation axes (e.g., the rotation and deflection axes). For example, catheter 12 may be mechanically oscillated about a second actuation axis and a third actuation axis by applying, respectively, a second oscillation vector at a second oscillation frequency and a third oscillation vector at a third oscillation frequency. The location of catheter 12 may be periodically measured in order to generate respective second and third pluralities of location data points, which may subsequently be processed using a signal processing algorithm in order to generate transfer functions relating a position of catheter 12 to a movement vector for the second and third actuation axes. These transfer functions may be resolved into and expressed as calibration vectors for the second and third actuation axes.

One skilled in the art should recognize from this disclosure that the details of the process relative to the second and third actuation axes generally follow those discussed with respect to the first actuation axis. For example, the second and third pluralities of location data points may be measured at respective second and third sampling rates, which are preferably multiples of the second and third oscillation frequencies, respectively. Similarly, either or both of the second and third plurality of location data points may be stored to a buffer or other memory. It is also contemplated that the first, second, and third oscillation frequencies may be equal, and that the first, second, and third sampling rates may be equal. One skilled in the art should further recognize from this disclosure that the process is carried out independently for each of the actuation axes so as to beneficially isolate the transfer function and/or calibration vector for each of the actuation axes. If desired, these several transfer functions and/or calibration vectors can then be composited into a calibration matrix in step 200, and the calibration matrix may be utilized in directing catheter 12 to navigate through the patient, for example to deliver therapy or to perform a diagnostic procedure.

Figure 9A:
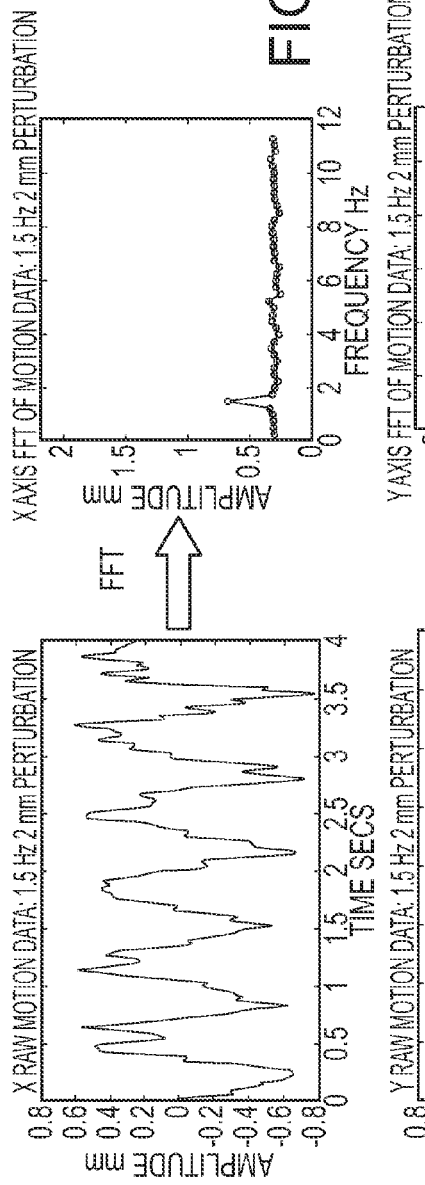
FIGS. 9a through 9c illustrate exemplary calibration plots, both as raw data and after signal processing, such as by application of a Fourier transform algorithm, on the x, y, and z measurement axes, respectively.
Figure 9B:
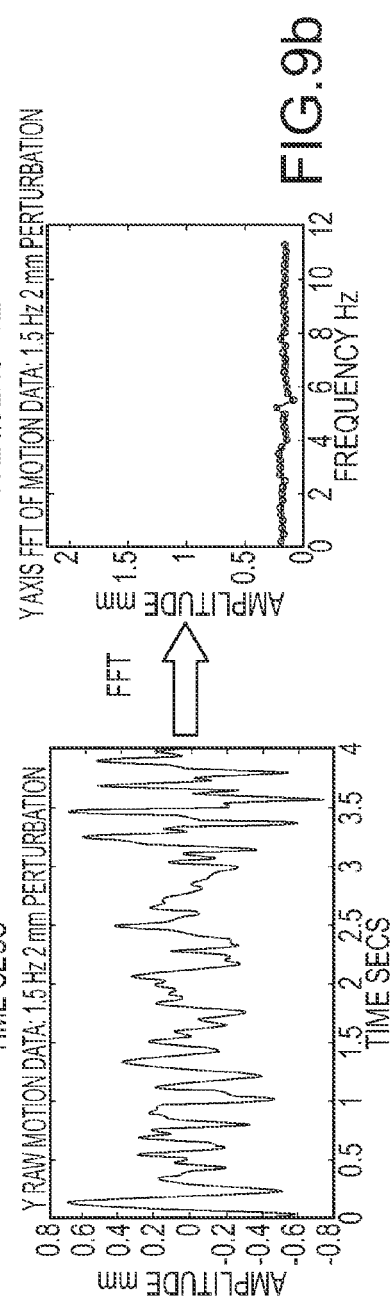
Figure 9C:
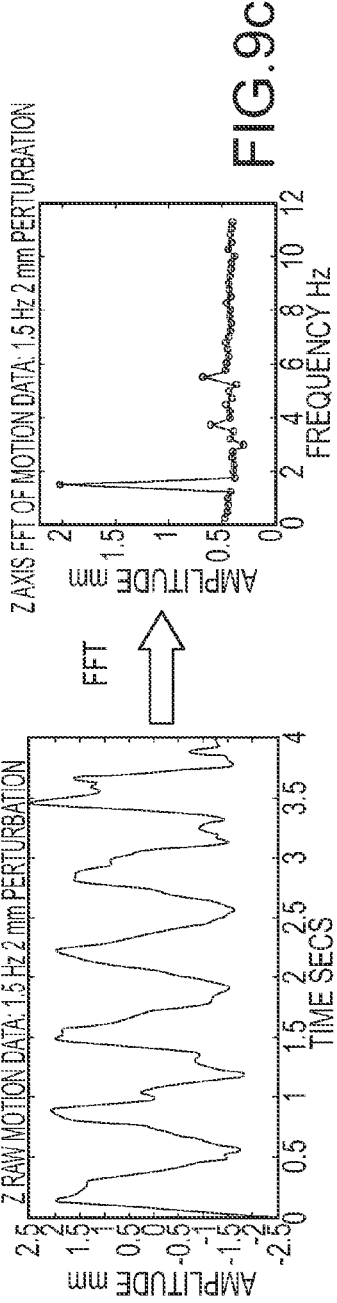

A working example of the present invention will now be described with references to FIGS. 9a through 9c. Catheter 12 is mechanically oscillated about an actuation axis, which may be translation, rotation, deflection, or otherwise, at a frequency of about 1.5 Hz for about 4 seconds, and the location of catheter 12 is measured in a Cartesian coordinate system as a function of time. The left-hand plots of FIGS. 9a through 9c depict the raw motion data (e.g., the plurality of location data points) as measured on the x, y, and z axes, respectively. The right-hand plots of FIGS. 9a through 9c depict the location data after signal processing using a Fourier transform algorithm. As seen in the Fourier transform plots, the 1.5 Hz frequency bin has an amplitude of 0.6 mm in the x direction, 0.2 mm in the y direction, and 2.0 mm in the z direction. Scaling to a 1 mm unit vector yields a calibration vector for the actuation axis shown of 0.29i+0.10j+0.95k.

Although an embodiment of this invention has been described above with a certain degree of particularity, those skilled in the art could make numerous alterations to the disclosed embodiment without departing from the spirit or scope of this invention. For example, though the present invention has been described in the context of a robotically controlled catheter, the calibration method disclosed herein could be practiced in the context of any other robotically controlled medical or non-medical devices incorporating a positional feedback system. Further, localization systems other than those discussed herein could be employed to periodically measure the location of the robotic device, including positional feedback systems that measure locations on other than an (x, y, z) coordinate system (e.g., a positional feedback system operating using parametric coordinates or displacement vectors).

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A robotic surgical system, comprising:
    a servo mechanism adapted to be coupled to a medical device such that the servo mechanism can induce the medical device to oscillate on a first axis;
    a positional feedback system adapted to output a first position signal representative of the position of at least one point on the medical device as the medical device oscillates on the first axis; and
    a processor to process the first position signal into a transfer function that relates inputs by the servo mechanism to movements of the medical device coupled thereto.

2. The robotic surgical system according to claim 1, further comprising a controller operably connected to the servo mechanism to energize the servo mechanism.

3. The robotic surgical system according to claim 1, wherein the servo mechanism comprises a translation servo mechanism and a deflection servo mechanism.

4. The robotic surgical system according to claim 3, wherein the servo mechanism further comprises a rotation servo mechanism.

5. The robotic surgical system according to claim 1, wherein the positional feedback system defines one or more measurement axes, and wherein the transfer function comprises a calibration vector including a component directed along each of the one or more measurement axes.

6. The robotic surgical system according to claim 1, wherein the positional feedback system is adapted to output the first position signal by periodically measuring the position of at least one point on the medical device as the medical device oscillates on the first axis.

7. The robotic surgical system according to claim 6, wherein a sampling rate at which the positional feedback system operates is an integer multiple of an oscillation frequency at which the servo mechanism operates.

8. An apparatus for calibrating a robotic surgical system including a servo mechanism operable to apply an oscillation vector to a medical device operably coupled thereto and a positional feedback system operable to output a position signal representative of a position of the medical device, the apparatus comprising:
    a position output processor configured to receive the position signal and generate a position output signal reflecting movement of the medical device attributable to the application of the oscillation vector; and
    a calibration processor configured to receive the position output signal and generate a transfer function that relates inputs to the servo mechanism to movements of the medical device operably coupled thereto.

9. The apparatus according to claim 8, wherein the position output processor applies a Fourier transform algorithm to the position signal.

10. The apparatus according to claim 8, wherein the position output processor applies a synchronous demodulation algorithm to the position signal.

11. The apparatus according to claim 8, wherein the position output processor applies a cross correlation algorithm to the first position signal.

12. An apparatus for calibrating a robotic surgical system including a servo mechanism and a positional feedback system, the apparatus comprising:
    a processor operably coupled to the robotic surgical system and configured to:
        energize the servo mechanism to apply an oscillation vector to a device coupled thereto;
        periodically measure a location of at least one point on the device while the oscillation vector is being applied to the device, thereby generating a position signal for the device;
        process the position signal to generate an output signal, wherein the output signal reflects movement of the device attributable to application of the oscillation vector to the device by the servo mechanism; and
        generate a transfer function from the output signal that relates inputs to the servo mechanism to resulting movements of the device.

13. The apparatus according to claim 12, wherein the oscillation vector is applied on a single axis selected from the group consisting of a translation axis, a rotation axis, and a deflection axis.

14. The apparatus according to claim 12, wherein the oscillation vector is applied to two or more axes selected from the group consisting of a translation axis, a rotation axis, and a deflection axis.

15. The apparatus according to claim 12, wherein the output signal is generated by applying a Fourier transform algorithm to the position signal.

16. The apparatus according to claim 12, wherein the output signal is generated by applying a synchronous demodulation algorithm to the position signal.

17. The apparatus according to claim 12, wherein the output signal is generated by applying a cross correlation algorithm to the position signal.

* * * * *